United States Patent [19]
Vallelunga et al.

[11] Patent Number: 5,738,655
[45] Date of Patent: Apr. 14, 1998

[54] NONREFILLABLE SYRINGE

[76] Inventors: Anthony J. Vallelunga, 213 Schoolhouse Rd., Albany, N.Y. 12203; Thomas E. Ferari, 7 Mohawk Trail, Queensbury, N.Y. 12804; James L. Kloss, 213 Schoolhouse Rd., Albany, N.Y. 12203

[21] Appl. No.: 680,169

[22] Filed: Jul. 15, 1996

[51] Int. Cl.⁶ ............................ A61M 5/00
[52] U.S. Cl. .............. 604/110; 604/218; 604/228
[58] Field of Search ................. 604/110, 218, 604/228, 187, 200, 229; 128/919

[56] References Cited

U.S. PATENT DOCUMENTS

| | | | |
|---|---|---|---|
| 5,078,686 | 1/1992 | Bates | 604/228 |
| 5,195,975 | 3/1993 | Castagna | 604/228 |
| 5,215,524 | 6/1993 | Vallelunga et al. | 604/228 |
| 5,226,882 | 7/1993 | Bates | 604/228 |
| 5,352,203 | 10/1994 | Vallelunga et al. | 604/110 |
| 5,411,489 | 5/1995 | Pagay et al. | 604/220 |
| 5,478,314 | 12/1995 | Malenchek | 604/228 |

*Primary Examiner*—Michael Powell Buiz
*Assistant Examiner*—Ronald K. Stright, Jr.
*Attorney, Agent, or Firm*—John A. Merecki

[57] ABSTRACT

A nonrefillable syringe including a unique plunger stem/piston arrangement which is designed to disconnect after an injection has been completed. A piston is removably connected to a plunger stem by a first connecting member and a novel nipple assembly. The first connecting member comprises a plurality of circumferentially spaced arms extending longitudinally away from the piston and forming an interior aperture. The nipple assembly includes a tapered nipple removably matable with the aperture formed by the circumferentially spaced arms of the first connecting member, and a cylindrical carrier for slidably positioning the nipple assembly within a hollow end of the plunger stem. The tapered nipple is gradually forced out of the aperture during use of the syringe. When the tapered nipple is forced completely out of the aperture, the piston disconnects from the plunger stem.

13 Claims, 6 Drawing Sheets

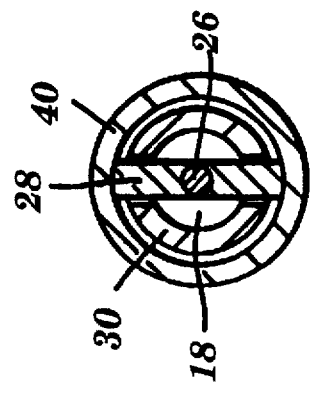
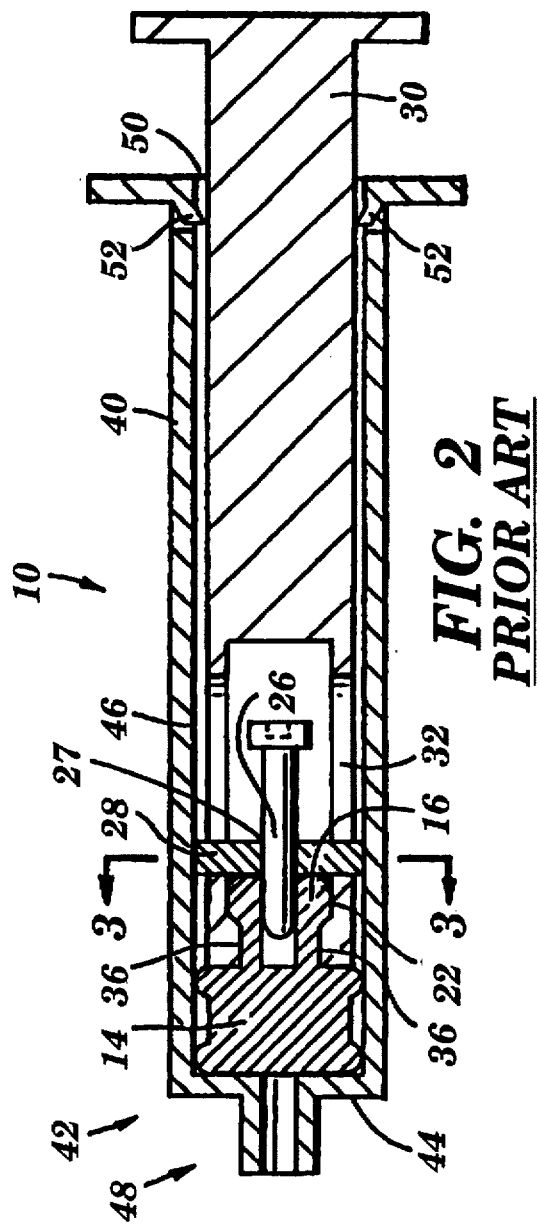
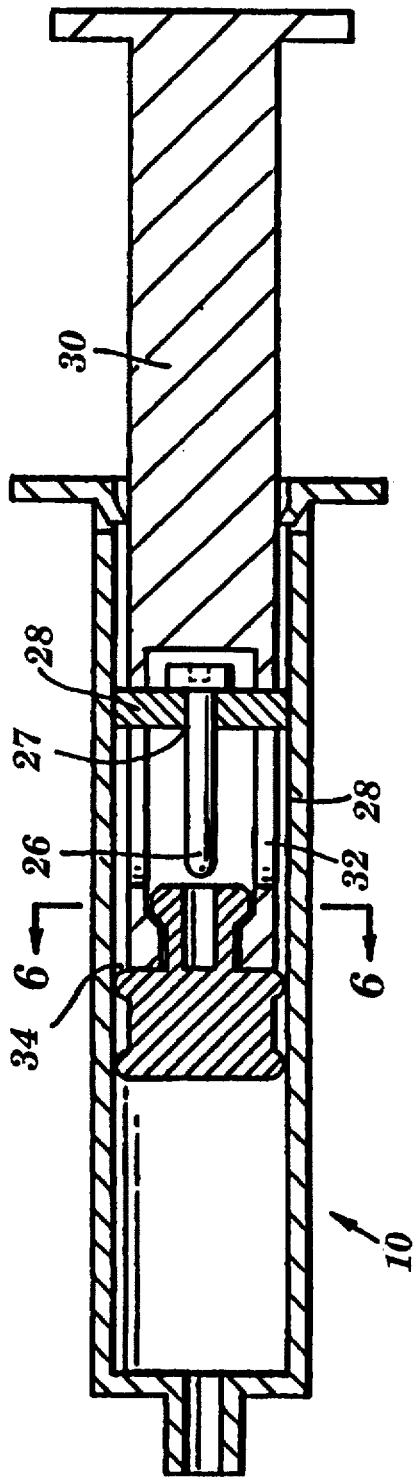

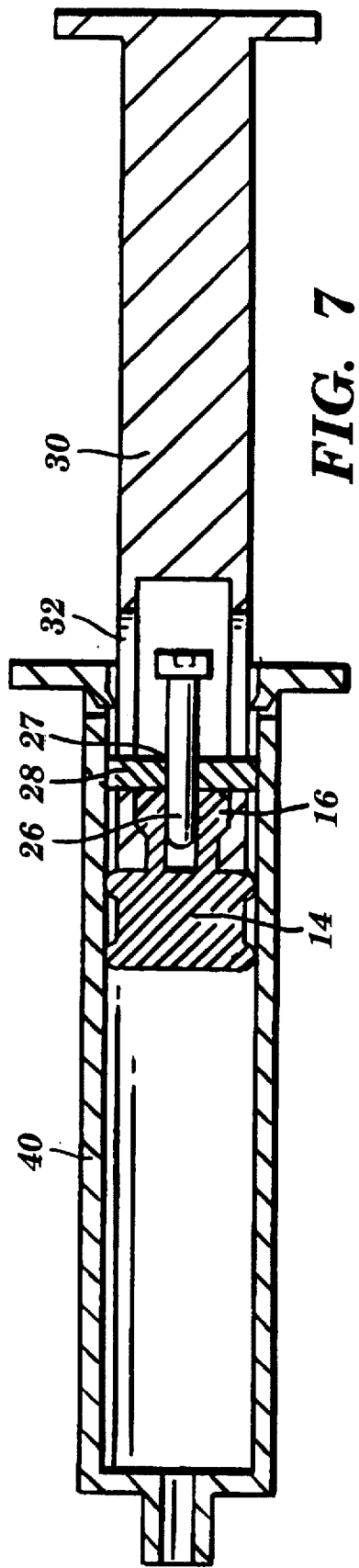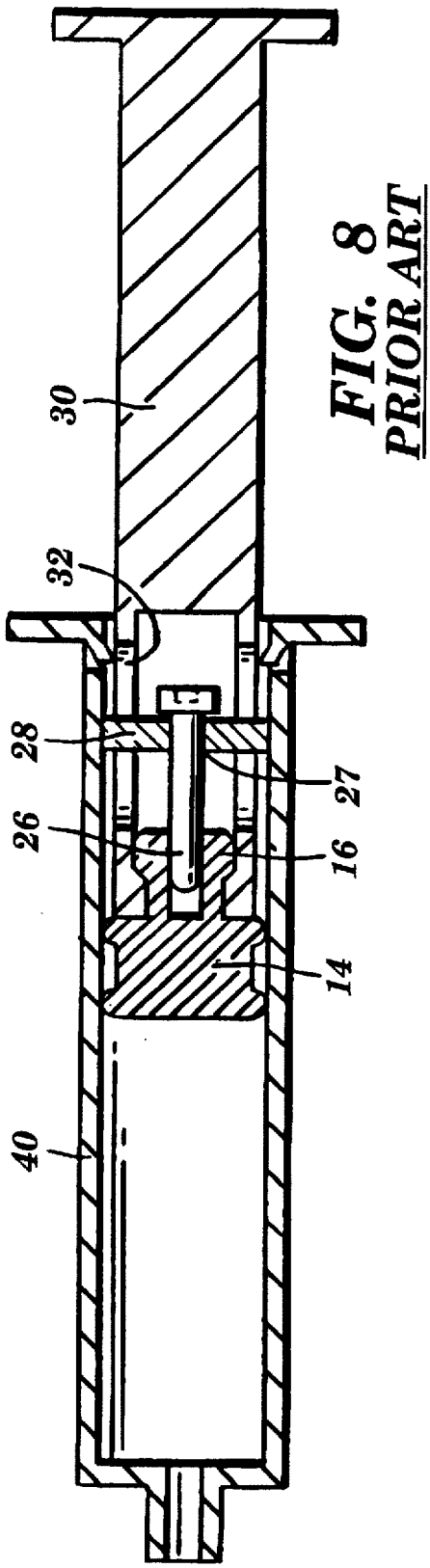

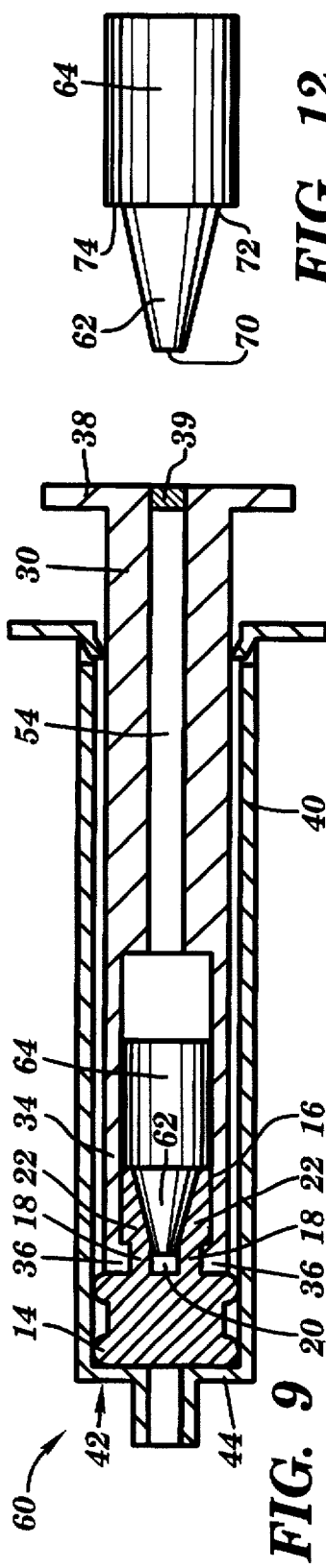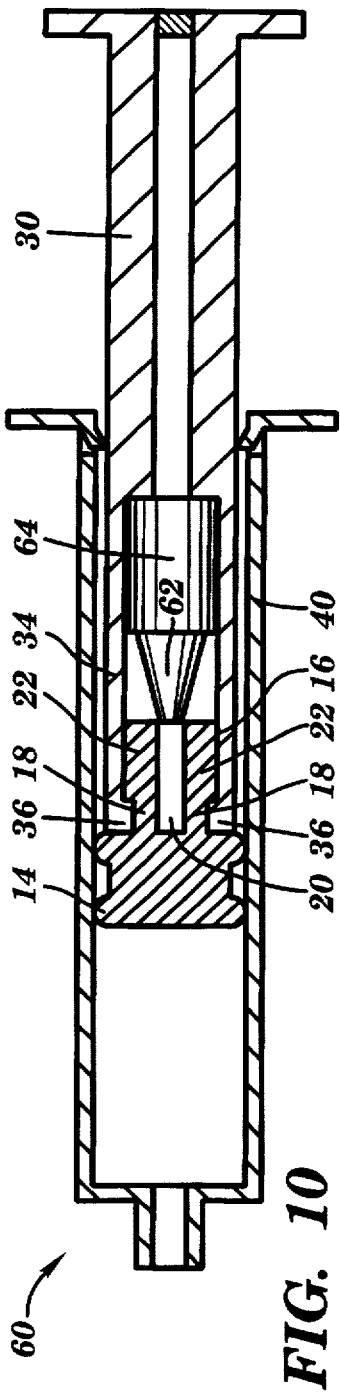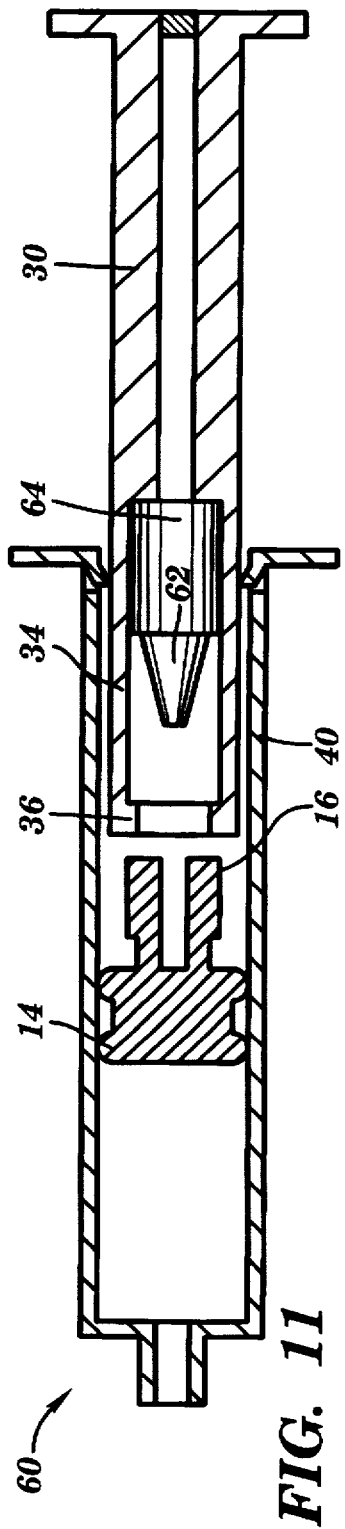

FIG. 13
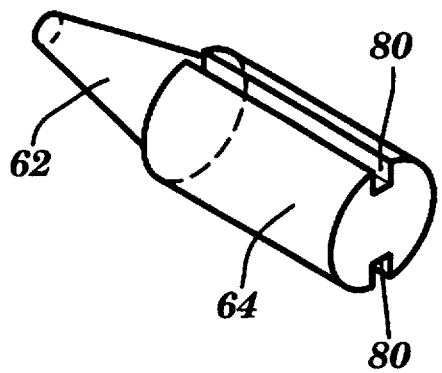
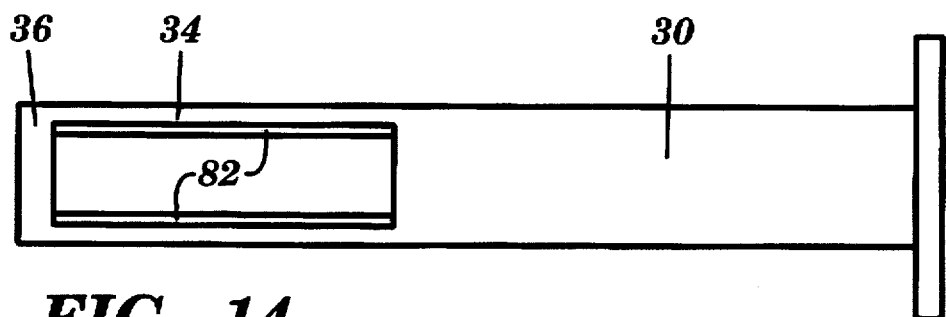
FIG. 14
FIG. 15
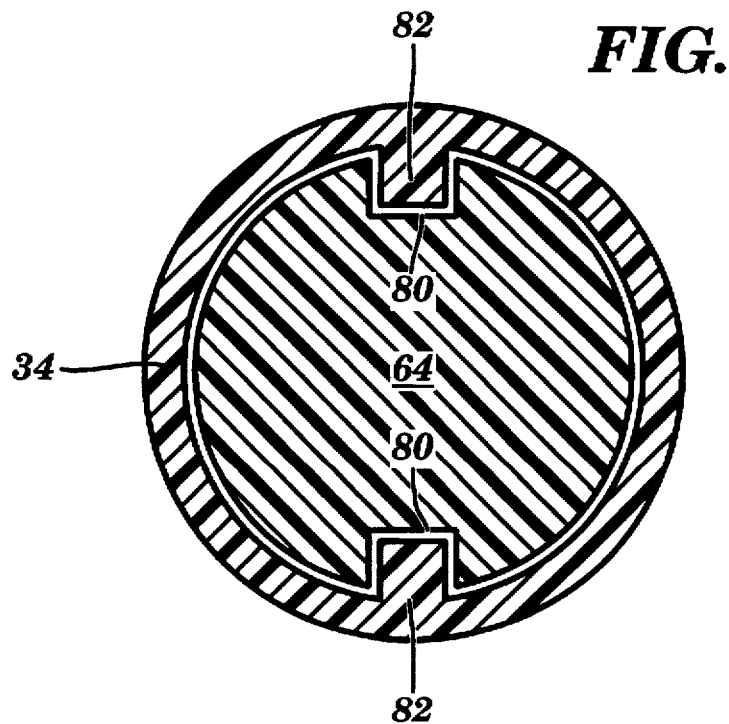

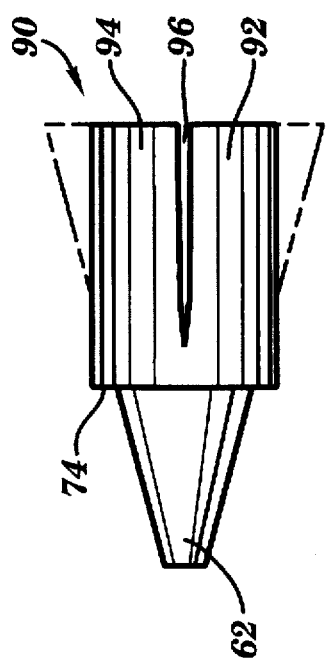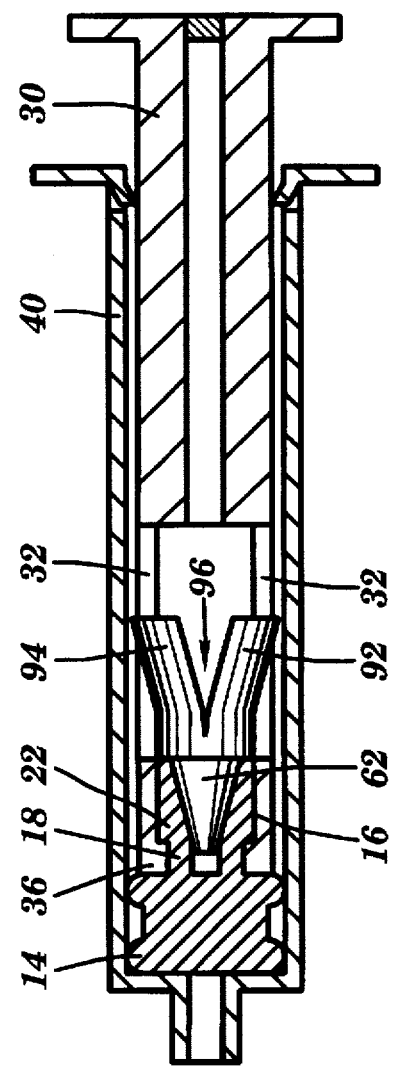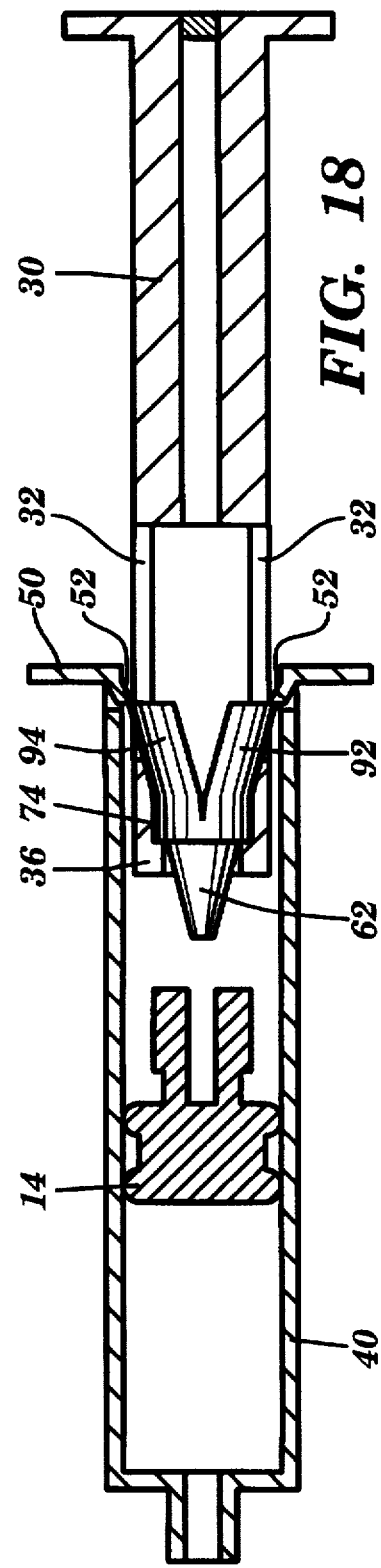

NONREFILLABLE SYRINGE

FIELD OF THE INVENTION

The present invention relates in general to a plunger for a nonrefillable/nonreusable syringe, and more particularly to a nonrefillable syringe which operates in the same manner as a conventional syringe, yet is incapable of being used more than once for making an injection. In a first prior art embodiment of the invention, as disclosed in U.S. Pat. No. 5,352,203, incorporated herein by reference, the nonrefillable syringe utilizes a plunger that includes three connecting members which disconnect the plunger stem from the plunger piston after an injection. In a second embodiment of the invention, the nonrefillable syringe utilizes a unique nipple assembly to disconnect the plunger stem from the plunger piston a after an injection, preventing further use of the syringe.

BACKGROUND OF THE INVENTION

In the United States and throughout the world, the multiple use of hypodermic syringe products which are intended for single use only is instrumental in drug abuse and more particularly in the transfer of contagious diseases. Such contagious diseases include AIDS and hepatitis. The transfer is most prevalent in intravenous drug users who routinely share and reuse syringes, but can also be a problem for the medical community if proper precautions to prevent multiple use of disposable syringes are not followed. Furthermore, the effects of multiple use are a major concern in third world countries where repeated use of syringe products may also be responsible for the spread of many diseases.

Many attempts have been made to remedy this problem. Some early attempted solutions involved destruction of the syringe after use either by using a destructive device or providing a syringe assembly with frangible zones so that the syringe could be rendered inoperable by the application of force. Although many of these devices work quite well, they require the specific intent of the user followed by the actual act to destroy or render the syringe inoperable. None of these devices is effective with a user having the specific intent to reuse the syringe.

Accordingly, there is a need for a nonrefillable syringe which becomes inoperative or incapable of further use automatically without an additional act on the part of the user. Co-owned U.S. Pat. No. 5,215,524, issued Jun. 1, 1993, the contents of which are hereby incorporated by reference, discloses a single use syringe which utilizes a disconnecting plunger stem. This syringe becomes inoperative automatically after a single use.

However, the need for a nonrefillable syringe must be met without preventing the filling or use of the syringe under normal conditions. One such use under normal conditions includes the ability to aspirate fluid using the syringe. It is common in the medical community to aspirate fluid during the use of a syringe (i.e., to alternately retract and extend the plunger of the syringe without expelling all contents of the syringe). This ability to aspirate must still be available with a single use syringe, and is not available with the syringe of U.S. Pat. No. 5,215,524.

Although various types of single use nonrefillable syringes have been proposed, the severity of the AIDS epidemic and the need for solutions to the above problems continuously provide a need for other types of nonrefillable syringes, particularly those which also provide for aspiration.

SUMMARY OF THE PRESENT INVENTION

In order to prevent the multiple use of a syringe, the first embodiment of the present invention provides a novel syringe which is incapable of being used more than once for making an injection and yet is capable of aspirating fluids. The nonrefillable syringe utilizes a plunger that includes three connecting members which disconnect the plunger stem from the plunger piston after insertion of the plunger into the housing of the syringe in order to expel the contents of the syringe.

The main components of the plunger of the subject invention include a piston and a cylindrical plunger stem hollow at an open end thereof. The piston is removably connected to the cylindrical plunger stem by first, second, and third connecting members. The first connecting member is connected longitudinally to the piston and extends into the open end of the plunger stem. The first connecting member comprises a plurality of circumferentially spaced arms extending longitudinally away from the piston. The circumferentially spaced arms form a first aperture in an interior thereof and are flared at an exterior thereof on an end opposite the connection to the piston. The second connecting member comprises a plurality of protrusions extending radially away from a second aperture. The third connecting member is a longitudinal nipple slidable within the second aperture and matable with the first aperture formed by the circumferentially spaced arms of the first connecting member. The cylindrical plunger stem has a plurality of circumferentially spaced slots extending longitudinally at an open end thereof, and the open end of the hollow cylindrical plunger stem encloses the first, second and third connecting members such that the plurality of protrusions of the second connecting member slide within the plurality of slots and are friction fit within the inner diameter of an outer housing.

To accomplish the nonrefillable feature of the syringe which includes the plunger of the subject invention, an open end of the plunger stem is constricted on an interior thereof such hat the interior snugly mates with flared exterior of the circumferentially spaced arms when the nipple is inserted into the first aperture formed by the interior thereof.

When the piston which is located at the front end of the plunger is inserted into the rear end of a hollow cylindrical housing of a syringe unit, the wall and the piston form a sealed cavity (with the cylindrical housing side wall) for containing a liquid within the interior of the syringe housing.

Prior to use, and preferably during manufacturing, the nipple is mated with the first aperture. When the nipple is mated with the first aperture, the second connecting member is positioned toward the front of the slots in the plunger stem. This allows the entire plunger unit to be drawn back for filling of the syringe, because in this configuration, the interior constricted portion of the cylindrical plunger stem exerts pressure on the circumferentially spaced arms. However, the nipple counteracts such pressure and prevents flexion of the arms inward. Therefore, the piston, plunger stem, and first, second and third connecting members operate as a single unit.

However, he nipple is forced from the first aperture as the protrusions on the second connecting member slide to the rear of the slots in the plunger stem. Any subsequent attempt to draw back the plunger to fill the syringe with fluid results in the interior constricted portion of the cylindrical plunger stem exerting pressure on the circumferentially spaced arms. Since the nipple no longer counteracts such pressure, the arms flex inward and the cylindrical plunger stem passes over the first connecting member. Thus, the plunger stem, second connecting member, and third connecting member are disconnected from the piston and the first connecting member. Accordingly, the syringe is incapable of being refilled because the piston must be withdrawn to create the vacuum for filling the syringe and to create the cavity for holding the liquid within the syringe.

The resulting nonrefillable single use syringe can thus be used to prevent multiple use of syringes, such as disposable hypodermic syringes. This is accomplished by providing the piston/syringe as discussed in further detail below.

The syringe according to the first embodiment of the present invention is also capable of aspiration due to the use of the sliding third connecting member (the nipple) within the second aperture. The nipple can slide within the aperture a distance equal to the length of the slots before the second connecting member (the plurality of protrusions) contacts the end of the slots and thereby forces the nipple out of the first aperture. Thus, one is able to move the plunger back and forth within the limitations of the slot length without disengaging the plunger stem. This allows for aspiration using the syringe as is also discussed in further detail below.

The aspirating, nonrefillable syringe of the first embodiment of the present invention provides an excellent solution to the problem of syringe refilling and reuse. However, this syringe cannot be used exactly like a conventional syringe. Specifically, when this syringe is used to inject air into a vial of medication to break the vacuum therein and fill the syringe with medication, the plunger stem may prematurely disconnect from the plunger piston prior to a subsequent injection.

The second embodiment of the present invention solves this problem by providing a nonrefillable syringe which functions exactly like a conventional syringe. During a typical injection, for example, the plunger stem/piston arrangement of this syringe is drawn back to fill the syringe housing with air. The air is subsequently injected into a vial of medication to break the vacuum. Thereafter, the syringe is filled with medication and aspirated in a known manner, and the medication is injected into a patient. After the injection has been completed, the plunger stem disconnects from the plunger piston rendering the syringe inoperable.

The second embodiment of the nonrefillable syringe of the present invention includes a unique plunger stem/piston arrangement which is designed to disconnect only after an injection has been fully completed. The main components of the plunger stem/piston arrangement include a piston and a cylindrical plunger stem hollow at an open end thereof. The piston is removably connected to the cylindrical plunger stem by the above-described first connecting member and a novel nipple assembly. The first connecting member is connected longitudinally to the piston and extends into the open end of the plunger stem. The first connecting member comprises a plurality of circumferentially spaced arms extending longitudinally away from the piston. The circumferentially spaced arms of the first connecting member form an interior aperture, and are flared at an exterior thereof on an end opposite the connection to the piston. The nipple assembly includes a tapered nipple removably matable with the aperture formed by the circumferentially spaced arms of the first connecting member, and a cylindrical carrier for slidably positioning the nipple assembly within the hollow end of the plunger stem. The open end of the plunger stem is constricted such that the interior snugly mates with the flared exterior of the circumferentially spaced arms when the tapered nipple is inserted into the aperture.

Prior to an injection, the tapered nipple of the nipple assembly is fully disposed within the first aperture formed between the circumferentially spaced arms of the first connecting member. During the use of the syringe, the drag of the piston against the interior surface of the syringe housing forces the flared ends of the circumferentially spaced arms against the constricted open end of the plunger stem as the piston is drawn out of, or pushed into, the syringe housing. This forces the flared ends of the circumferentially spaced arms against the nipple, exerting an overall rearward force against the nipple disposed within the aperture. Ultimately, after the injection has been fully completed, the nipple is forced out of the aperture by the rearward force applied by the circumferentially spaced arms as the piston is displaced within the syringe. At this point, the arms of the first connecting member flex inward due to the absence of the nipple, causing the piston to disconnect from the plunger stem.

BRIEF DESCRIPTION OF THE DRAWINGS

These and other objects, features and advantages of the present invention will be evident from the following detailed description of preferred embodiments when read in conjunction with the accompanying drawings in which:

FIG. 2 is a side view of a nonrefillable syringe including the plunger shown in FIG. 1, shown prior to withdrawal of the plunger to fill the syringe;

FIG. 3 is a cross-sectional view of the nonrefillable syringe shown in FIG. 2;

FIG. 5 is a side view of the nonrefillable syringe of FIG. 2 indicating the position of the syringe elements during insertion of the plunger into the hollow cylindrical housing of the syringe;

FIGS. 7 and 8 are side views of the nonrefillable syringe of FIG. 2 showing the aspiration feature of the syringe accomplished by sliding the nipple within the aperture without disconnecting the nipple from the aperture;

FIG. 9 is a cross-sectional view of a nonrefillable syringe according to a second embodiment of the present invention, with the piston connected to the plunger stem;

FIG. 10 illustrates the nonrefillable syringe of FIG. 9 as the piston disconnects from the plunger stem after the completion of an injection;

FIG. 11 illustrates the nonrefillable syringe of FIG. 9 with the piston completely disconnected from the plunger stem;

FIG. 12 shows an enlarged view of the nipple assembly used within the nonrefillable syringe illustrated in FIGS. 9–11;

FIG. 13 illustrates an alternate embodiment of the nipple assembly;

FIG. 14 illustrates an alternate embodiment of the plunger stem;

FIG. 15 is a cross-sectional view of the nipple assembly of FIG. 12, illustrating the coaction of the grooves 80 and complementary runners 82;

FIG. 16 shows another alternate embodiment of the nipple assembly, wherein the carrier is configured to lock the plunger stem within the syringe housing after use;

FIG. 17 is a cross-sectional view of a nonrefillable syringe incorporating the nipple assembly of FIG. 16; and FIG. 18 illustrates the locking action provided by the carrier of the nipple assembly of FIG. 16.

DETAILED DESCRIPTION OF THE INVENTION

Figure 1:
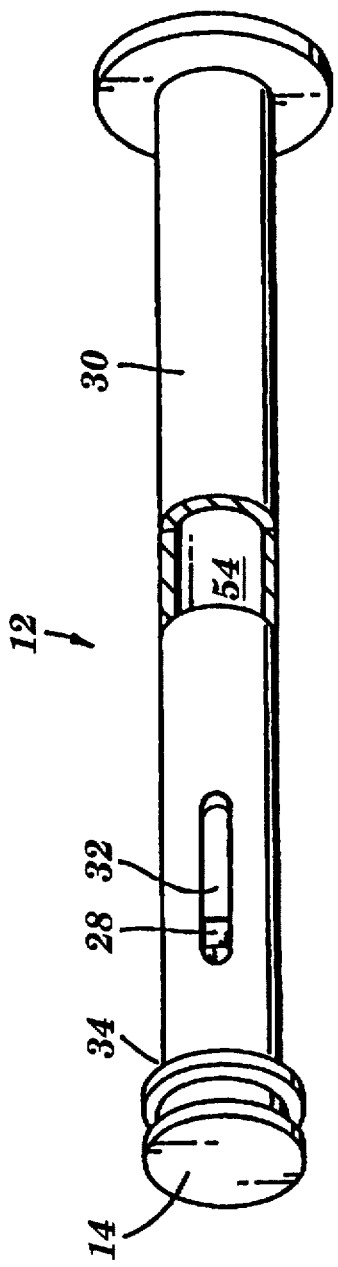
FIG. 1 is a partially cut away isometric view of a plunger which is a prior art embodiment of the subject invention.
Figure 4:
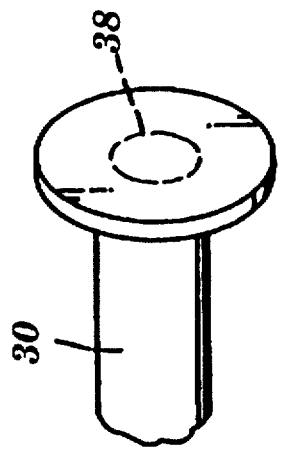
FIG. 4 is a partial isometric view of the rear end of the plunger shown in FIG. 1.

The main components of the first embodiment of the subject invention are depicted in FIGS. 1–8. As shown in FIGS. 1 and 4, the plunger 12 comprises a cylindrical plunger stem 30 closed at its rear end 38 and hollow at least at the other front end 34. At the front end 34 of the plunger stem 30 a piston 14 provides a liquid sealing means. The closed rear end 38 and the piston 14 form an interior 54 of the plunger 12. Toward the front end 34 of the plunger 12, slots 32 extend longitudinally around the circumference of the plunger stem.

Figure 6:
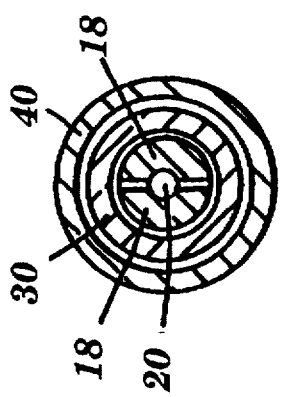
FIG. 6 is a cross-sectional view of the nonrefillable syringe shown in FIG. 5.

The plunger stem 30 is connected to the piston 1 by a first connecting member 16, a second connecting member (made up of aperture 27 and protrusions 28), and a third connecting member comprising a longitudinal nipple 26. As shown in FIGS. 2 and 6, the first connecting member 16 is connected longitudinally to the piston 14, or may be integral therewith, and comprises a plurality of circumferentially spaced arms 18 extending longitudinally away from the piston 14. The arms 18 form a first aperture 20 at their interior, the purpose of which is discussed in further detail below. At the exterior end 22 of the arms away from the connection to the piston, the arms are flared. The first aperture 20 is mated with the third connecting member, a longitudinal nipple 26 having a tapered end. The second connecting member includes a plurality of protrusions 28 which extend radially away from a second aperture 27 to form a friction fit within the inner diameter of an outer housing (see below) and also slidably fit within the slots 32 of the plunger stem 30. This is best shown in FIGS. 2 and 3. The nipple 26 slides within this second aperture 27. The interior surface at the front end of the plunger stem forms a constricted end 36, such that the front end 34 of the plunger stem 30 snugly fits against the arms 18 of the first connecting member 16. The flared end 22 of the first connecting member 16 mates with the constricted end 36 of the interior of the plunger stem 30 (see FIG. 2).

The plunger 12 is snugly inserted into a syringe housing 40 of a syringe 10 (see FIGS. 2 and 5). The syringe housing 40 is closed at its front end 42 by a wall 44, to which a needle can be mounted via a mounting means 48. Syringe needles are generally marketed with a plastic-type bracket on end thereof. This plastic-type bracket mounts to the mounting means 48. The bracket may snugly slide over the mounting means 48, or the mounting means could be provided with grooves into which corresponding ridges on the bracket are twisted. Various means for connecting the syringe needles are known in the art and can thus be used in the subject invention to mount a needle to the mounting means. A needle so mounted in the wall 44 is in fluid communication with the interior 46 (see FIG. 2) of the syringe housing 40.

In order to prevent tampering with the connecting members in an attempt to reuse the syringe, removal of the plunger 12 is prevented by a circumferential, one-way flange 52 at the rear end 50 of the syringe housing 40. This flexible flange is angled so that insertion of tile plunger is possible but removal is not possible due to the contact of the protrusions 28 of the second connecting member with the flange 52. Specifically, the diameter of the second connecting member protrusions 28, which are friction fit within the syringe housing 40, is such that the second connecting member cannot pass through the housing at the position of the flange 52.

Having described one embodiment of the plunger and nonrefillable syringe of the subject invention, its use is best illustrated in FIGS. 2 and 5, and 7 and 8. As shown in FIG. 2, the initial position of the elements of the syringe 10 prior to withdrawal (so as to fill the syringe) are illustrated. The plunger 12 is fully inserted into the syringe housing 40, such that the piston 14 is adjacent the wall 44 at the front end 42 of the housing 40. The nipple 26 is mated with the aperture 20 and the protrusions 28 are positioned slidably within and toward the front of the slots 32. A cross-section illustrating the position of the syringe elements taken through the second connecting member is shown in FIG. 3. In this position, the nipple 26 prevents withdrawal of the plunger stem 30 without simultaneous withdrawal of the piston 14. This is because withdrawal of the plunger stem 30 causes the constricted front end 36 of the plunger stem 30 to exert a rearward force on the flared ends 22 of the first connecting member's arms 18. The nipple 26 prevents the arms 18 from flexing inward in response to this force. Accordingly, the entire plunger 12 unit is pulled rearward in one motion, so as to fill the syringe.

Upon forward motion of the plunger stem 30 to an extent greater than the length of the slot 32, as shown in FIG. 5, the second connecting member including the plurality of protrusions 28 slides to the rear of the slots 32 and the nipple 26 is no longer mated with the aperture 20. FIG. 6 illustrates a cross-section of the syringe at the position of the flared ends of the arms at this point of an injection stroke. Any subsequent rearward movement of the plunger stem therefore results in another rearward force on the flared ends of the first connecting member's arms. The removal of the nipple allows the arms to flex inward, allowing the constricted end of the plunger stern to pass thereby. The plunger stem, second connecting member, and third connecting member are thus withdrawn, but the piston and first connecting member remain within the housing and no longer operate in conjunction with the plunger stem. As should be readily apparent, the syringe is then incapable of being used again because the movement of the piston is necessary to create the vacuum for filling of the syringe.

FIGS. 7 and 8 illustrate the aspiration feature of the subject invention. The syringe (beginning as show, n in FIG. 2) plunger stem 30 is withdrawn in the syringe housing 40 to the point shown in FIG. 7. The plunger stem 30 is then pushed back into the syringe housing 40 to the position shown in FIG. 8. At this point, the nipple 26 remains mated within the first aperture 20 of the first connecting member 16, by sliding within the second aperture 27 of the second connecting member. The plunger stem 30 can be alternately withdrawn and pushed into the syringe 40 in this fashion for aspiration until the plurality of protrusions 28 of the second connecting member contact the rear of the slots 32. At that time, the second connecting member will pull the nipple 26 out of the first aperture 20 of the first connecting member 16 and render the syringe incapable of further use, as shown in FIG. 5.

Thus, the amount of aspiration possible can be controlled by controlling the length of the slots and the length of the longitudinal nipple. By extending the slot and providing a nipple which can slide within the second connecting member, this aspiration feature is attainable.

It should be readily apparent to those skilled in the art that any suitable materials, such as plastic and rubber, can be utilized for the various syringe elements.

The syringe which includes the plunger as described above is assembled as follows. The piston 14 and the first connecting member 16 are positioned at the front end 42 of the syringe housing 40. The nipple 26 is positioned in the aperture 27 of the second connecting member, and both members so connected are then positioned within the cylindrical plunger stem 30 so that the protrusions 28 of the second connecting member extend through the slots 32 of the cylindrical plunger stem 30. At this point, the rear end 38 of the plunger stem 30 is not closed or sealed, but remains hollow (see broken lines on FIG. 4). The hollow cylindrical plunger stem 30, with the second and third connecting members positioned within the plunger stem, is snugly inserted into the syringe housing 40 until the nipple 26 contacts the first connecting member 16 at the front of the syringe housing 40. A rigid device, such as a wire or even a pencil-like member, is inserted into the hollow center 54 of the plunger stem 30 to exert a forward force on the nipple 26. This causes the nipple 26 to mate with the first aperture 20 of the first connecting member 16. The rigid device is then removed from the center of the plunger stem, and the rear end 38 of the plunger stem is sealed or closed by suitable means. For example, a plastic plug may be inserted or injected, or a cap can be permanently applied plunger stem. The plunger stem. The end is permanently sealed so that future tampering with the second and third connecting members is not possible. This prevents the syringe from being "reset", i.e., by forcing the third connecting member nipple forward to mate with the first aperture. After the end of the plunger stem is sealed, the syringe is ready for use. Accordingly, after any required aspiration and a single dispensing use, the syringe of the subject invention cannot be used again because the plunger stem separates from the piston. This prevents subsequent filling with liquid.

The first embodiment of the subject invention thus provides a method of preventing multiple use of a syringe comprising the steps of: selecting the single use syringe of the subject invention as disclosed above; drawing a liquid into the single use syringe; and dispensing the liquid from the single use syringe. When the liquid has been dispensed from the single use syringe, the syringe cannot again be used to draw a liquid into the syringe due to the separation of the piston from the plunger stem upon any subsequent withdrawal of the plunger body. The invention also provides a method of aspirating using a single use syringe by alternately pushing and drawing the plunger without unmating the nipple of the syringe.

The operation and structure of the nonrefillable syringe 60 in accordance with the second embodiment of the present invention is illustrated in FIGS. 9–11. The syringe 60 is generally similar in construction to the previously-described syringe 10. However, a novel nipple assembly, comprising a tapered, conically-shaped nipple 62 and a cylindrical carrier 64, is used in lieu of the nipple 26 and protrusions 28 of the syringe 10 to effect the disconnection of the piston 14 from the plunger stem 30 in the syringe 60. For simplicity, only those reference numerals required to describe the differences in structure and operation of the syringe 60 have been illustrated in FIGS. 9–11.

An enlarged view of the nipple assembly is shown in FIG. 12. The nipple assembly includes the tapered nipple 62 and the cylindrical carrier 64. As illustrated, the diameter of the tapered nipple 62 gradually increases from a first end 70 to a second end 72 connected to the cylindrical carrier 64. The diameter of the second end 72 of the tapered nipple 62 is preferably slightly smaller than the diameter of the cylindrical carrier 64, thereby forming a circular rim 74. The first end 70 of the tapered nipple 62 can be flat as illustrated in FIG. 12, or may be slightly rounded. Preferably, the tapered nipple 62 and cylindrical carrier 64 are formed as a single unit. However, the tapered nipple 62 and cylindrical carrier 64 can be formed separately and subsequently joined in any suitable manner to form the nipple assembly of the present invention. As will be come more apparent hereinbelow, the degree of taper of the nipple 62 can be adjusted to control the timing of the disconnection of the piston 14 from the plunger stem 30. Additionally, although a tapered nipple is preferred, the nipple 62 can be formed without a taper (i.e., cylindrical) without departing from the scope of the present invention.

As illustrated in FIG. 9, the first connecting member 16 is connected longitudinally to the piston 14, or may be integral therewith, and comprises a plurality of circumferentially spaced arms 18 extending longitudinally away from the piston 14. The arms 18 form an interior aperture 20. At the end 22 of the arms 18 away from the connection to the piston, the arms are flared. The first aperture 20 is designed to be removably mated with the tapered nipple 62 of the nipple assembly.

The initial position of the elements of the syringe 60 prior to a withdrawal of the piston (e.g., to fill the syringe with air or medication) is illustrated in FIG. 9. Specifically, the plunger is fully inserted into the syringe housing 40, with the piston 14 positioned adjacent the wall 44 at the front end 42 of the housing 40, and the flared ends 22 of the arms 18 of the first connecting member 16 mated with the constricted end 36 of the interior of the plunger stem 30. The nipple assembly is positioned within the hollow front end 34 of the plunger stem 30 such that the entire length of the nipple 62 is positioned within the aperture 20, with the rim 74 of the carrier 64 abutting the flared ends 22 of the arms 18 of the first connecting member 16. In this position, the nipple 62 prevents withdrawal of the plunger stem 30 without simultaneous withdrawal of the piston 14. This occurs because withdrawal of the plunger stem 30 causes the constricted front end 36 of the plunger stem 30 to exert an inward force on the flared ends 22 of the arms 18 due to the drag of the piston 14 within the syringe housing 40. The nipple 62 prevents the arms 18 from flexing inward in response to this force. Accordingly, the entire plunger unit can be pulled rearward as a unit to fill the syringe 60 with air or medication, or during aspiration.

The inward force applied by the flared ends 22 of the arms 18 against the tapered nipple 62 is partially converted into a rearward force due to the taper of the nipple. This rearward force displaces the nipple 62 partially out of the aperture 20 formed by the arms 18 of the first connecting member 16. Each time the piston 14 is pulled out of the syringe housing 40 during an injection process, the nipple 62 is forced further out of the aperture 20.

When the piston 14 is pushed into the syringe housing 40 by the plunger stem 30, e.g., to inject air into a vial of medication, to perform aspiration, or to inject medication into a patient, the drag of the piston 14 against the interior surface of the housing 40 forces the flared ends 22 of the circumferentially spaced arms 18 of the first connecting member 16 rearwardly away from the constricted open end 36 of the plunger stem 30. This rearward force is transferred to the tapered nipple 62 enclosed within the aperture 20 formed by the arms 18, again forcing the nipple 62 partially out of the aperture 20. Each time the piston 14 is pushed into the syringe housing during the stages of an injection process, the nipple 62 is forced further out of the aperture 20.

When the nipple 62 is forced completely out of the aperture 20 (FIG. 10), the flared ends 22 of the arms 18 of the first connecting member 16 are no longer prevented from flexing inward as the piston 14 is withdrawn from the syringe housing 40. As a consequence, after the nipple 62 has been forced out of the aperture 20, any subsequent withdrawal of the piston 14 causes the piston 14 to disconnect from the plunger stem 30 (FIG. 11).

The syringe 60 is designed such that the disconnection of the piston 14 from plunger stem occurs after the completion of an injection. Thus, the syringe 60 provides the same functionality as a conventional syringe, yet disconnects after the completion of an injection to prevent the syringe from being refilled or reused. If, for some reason, the piston 14 has not yet disconnected from the plunger stem 30 after an injection, the plunger stem can be inserted into and/or withdrawn from the syringe housing 40 until the tapered nipple 62 is forced out of the aperture 20 formed by the arms 18 of the first connecting member 16.

The nonrefillable syringe 60 can be assembled as follows. The piston 14 and the first connecting member 16 are positioned within the front end 42 of the syringe housing 40. The nipple assembly is positioned within the hollow front end 34 of the plunger stem 30. At this point, the rear end 38 of the plunger stem 30 is not closed or sealed, but remains hollow. The plunger stem 30, with the nipple assembly positioned within the plunger stem, is inserted into the syringe housing 40 until the tapered nipple 62 contacts the legs 18 of the first connecting member 16 at the front of the syringe housing 40. A rigid device, such as a wire or the like, is inserted into the hollow center 54 of the plunger stem 30 to exert a forward force on the base of the cylindrical carrier 64 of the nipple assembly. This causes the nipple 62 to mate with the first aperture 20 of the first connecting member 16. The rigid device is then removed from the center of the plunger stem 30, and the rear end 38 of the plunger stem is sealed or closed by suitable means 39. For example, a plastic plug may be inserted or injected, or a cap can be permanently applied to the end of the plunger stem. The end is permanently sealed so that future tampering with the nipple assembly is not possible. This prevents the syringe from being "reset", i.e., by again forcing the tapered nipple 62 forward to mate with the aperture 20 formed by the legs 18 of the first connecting member. After the end of the plunger stem 30 is sealed, the syringe is ready for use.

An alternate embodiment of the nipple assembly is illustrated in FIG. 13. This embodiment of the nipple assembly again includes the tapered nipple 62 and the cylindrical carrier 64. However, at least one longitudinal guide groove 80 is additionally provided on the cylindrical carrier 64 to maintain the proper orientation of the nipple assembly within the hollow end 34 of the plunger stem 30. This is achieved by providing a corresponding number of longitudinally disposed, protruding runners 82 (FIG. 14) on the interior surface of the hollow end 34 of the plunger stem 30. Specifically, the nipple assembly is positioned within the hollow end 34 of the plunger stem 30 such that the runners 82 mate with a corresponding one of the guide grooves 80 (FIG. 15). In this way, the nipple assembly is constrained to move longitudinally within the hollow end 34 of the plunger stem 30 during the assembly and use of the nonrefillable syringe 60.

An alternate embodiment of the nipple assembly is illustrated in FIG. 16. Specifically, the nipple assembly includes the above-described tapered nipple 62, and a unique carrier 90 which provides the same function as the carrier 64, yet is configured to lock the plunger stem 30 within the syringe housing 4(7) after use. The carrier 90 includes a pair of opposing wings 92, 94 separated by a groove 96. The normal operational state of the carrier, with the wings 92, 94 spread apart, is shown in phantom in FIG. 16 and in operation in FIGS. 17 and 18. When the wings 92, 94 are pushed together, the carrier 90 assumes a substantially cylindrical shape, thereby allowing the carrier 90 to be inserted into the syringe housing 40 within the hollow end 34 of the plunger stem during assembly of the nonrefillable syringe.

The tapered nipple 62 operates as described above in conjunction with the piston 14 and first connecting member 16 to disconnect the piston 14 from the plunger stem 30 after the completion of an injection. Further, the carrier 90 operates in a manner similar to that of the carrier 64 (FIGS. 9–11) to slidably position the nipple assembly within the hollow end 34 of the plunger stem 30). However, as shown in FIGS. 17 and 18, the carrier 90 additionally serves to lock the plunger stem 30 within the syringe housing 40.

When positioned within the hollow open end 34 of the plunger stem, each wing 92, 94 extends freely through a corresponding one of the longitudinally extending slots 32 formed in the hollow open end 34 of the plunger stem 30. As shown in FIG. 17, the tips of the wings 92, 94 extend through the slots 32. However, the tips do not contact the interior surface of the syringe housing 40.

After the disconnection of the piston 14 from the plunger stem 30, and as the plunger stem 30 is withdrawn from the syringe housing 40, the wings 92, 94 of the carrier 90 engage the circumferential one-way flange 52 at the rear end 50 of the syringe housing 40. This causes the nipple assembly to slide forward within the hollow end 34 of the plunger stem 30 until the rim 74 of the carrier engages the constricted end 36 of the plunger stem 30 (FIG. 18). When in this position, the nipple assembly prevents further withdrawal of the plunger stem 30, effectively locking the plunger stem 30 within the syringe housing 40.

Although preferred embodiments have been depicted and described in detail herein, it will be apparent to those skilled in the relevant art that various modifications, additions, substitutions and the like can be made without departing from the spirit of the invention and these are therefore considered to be within the scope of the invention as defined in the following claims.

We claim:

1. A nonrefillable syringe comprising:

a syringe housing;

a plunger movably disposed within the interior of said syringe housing, said plunger comprising:

a plunger stem having a hollow end portion;

a piston attached to said plunger stem;

a first connecting member connected to said piston, said first connecting member comprising a plurality of arms extending longitudinally away from said piston into the hollow end portion of said plunger stem, said arms forming an aperture at an interior thereof;

a nipple assembly comprising a nipple removably matable with said aperture and a carrier for guiding said nipple longitudinally within the hollow end portion of said plunger stem, the arms of said first connecting member forcing said nipple out of said aperture as said piston is displaced within said syringe housing by said plunger stem, said piston disconnecting from said plunger stem after said nipple is forced out of said aperture; and means for guiding said nipple assembly longitudinally through the hollow end portion of said plunger stem, said guiding means including at least one groove formed on an exterior of said carrier, and at least one complementary runner, formed on an interior of the hollow end portion of said plunger stem, and slidably disposed within said groove, for guiding said nipple assembly longitudinally through the hollow end portion of said plunger stem.

2. The nonrefillable syringe according to claim 1, wherein the arms of said first connecting member include a flared exterior portion, and wherein the hollow end portion of said plunger stem includes an open end, constricted on an interior thereof, at least the flared exterior portion of the arms of said first connecting member extending into the hollow end portion of said plunger through the open end of said plunger stem.

3. The nonrefillable syringe according to claim 2, wherein, when said nipple is disposed within said aperture, the flared exterior portion of the arms of said first connecting member snugly mate with the constricted interior of said plunger stem, thereby preventing said piston from disengaging from said plunger stem.

4. The nonrefillable syringe according to claim 3, wherein, when said nipple is not disposed with said aperture, the flared exterior portion of the arms of said first connecting member pass through the open end of the hollow end portion of said plunger stem upon a withdrawal of said plunger stem, thereby disconnecting said piston from said plunger stem.

5. The nonrefillable syringe according to claim 1, wherein said nipple assembly further includes means for locking said piston stem within said syringe housing.

6. The nonrefillable syringe according to claim 5, wherein the carrier of said nipple assembly includes at least one wing for engaging a flange member on an interior surface of said syringe housing, thereby locking said piston stem within said syringe housing.

7. The nonrefillable syringe according to claim 6, wherein each said wing extends through a slot formed through the hollow end portion of said plunger stem.

8. The nonrefillable syringe according to claim 1, wherein said first connecting member is integral with said piston.

9. The nonrefillable syringe according to claim 1, wherein said nipple is tapered.

10. The nonrefillable syringe according to claim 1, wherein said nipple is tapered and said carrier is cylindrical, said tapered nipple including a first, distal end and a second end adjacent said carrier, said tapered nipple having a diameter that decreases from said second end to said first, distal end.

11. The nonrefillable syringe according to claim 1, wherein drag between said piston and an interior surface of said syringe housing causes the arms of said first connecting member to gradually force said nipple out of said aperture as said piston is displaced within said syringe housing by said plunger stem, said piston disconnecting from said plunger stem after said nipple is forced out of said aperture.

12. The nonrefillable syringe according to claim 1, wherein said piston disconnects from said plunger stem after completion of an injection.

13. The nonrefillable syringe according to claim 1, wherein said nonrefillable syringe further includes:

means for locking said piston stem within said syringe housing after an injection.

* * * * *